(12) United States Patent
Mao et al.

(10) Patent No.: US 12,674,753 B2
(45) Date of Patent: Jul. 7, 2026

(54) SAMPLE HOLDER FOR SURFACE PLASMON RESONANCE AND PLASMON-WAVEGUIDE RESONANCE APPARATUS

(71) Applicant: Mainline Scientific LLC, Malvern, PA (US)

(72) Inventors: Yousheng Mao, Hockessin, DE (US); Shouwen Xu, Shanghai (CN); Han Zhang, Williamsville, NY (US); Ting Wang, Berwyn, PA (US)

(73) Assignee: Mainline Scientific LLC, Malvern, PA (US)

( * ) Notice: Subject to any disclaimer, the term of this patent is extended or adjusted under 35 U.S.C. 154(b) by 1072 days.

(21) Appl. No.: 17/738,903

(22) Filed: May 6, 2022

(65) Prior Publication Data

US 2023/0358676 A1 Nov. 9, 2023

(51) Int. Cl.
G01N 21/552 (2014.01)
G01N 21/03 (2006.01)
G01N 33/543 (2006.01)

(52) U.S. Cl.
CPC ........... G01N 21/554 (2013.01); G01N 21/03 (2013.01); G01N 33/54373 (2013.01); *G01N 2201/068* (2013.01)

(58) Field of Classification Search
CPC .......... G01N 2021/0371; G01N 21/03; G01N 21/553; G01N 21/554; G01N 2201/068; G01N 33/54373

(Continued)

(56) References Cited

U.S. PATENT DOCUMENTS 5,521,702 A 5/1996 Salamon et al.
5,973,774 A * 10/1999 Haggett ................. G01N 21/43
356/135

(Continued)

FOREIGN PATENT DOCUMENTS

CN 110596052 A 12/2019
CN 210146038 U 3/2020

OTHER PUBLICATIONS

International Search Report and Written Opinion for PCT/US22/28173, Aug. 29, 2022.

(Continued)

*Primary Examiner* — Sunghee Y Gray
(74) *Attorney, Agent, or Firm* — Don D. Cha; HDC Intellectual Property Law LLP

(57) ABSTRACT

The present invention is directed to a removable sample holder for analytical instruments or apparatuses that utilizes a prism. For example, sample devices of the invention can be used in a surface plasmon resonance (SPR) spectroscopy, a plasmon-waveguided resonance (PWR) spectroscopic device, as well as other spectroscopy devices known to one skilled in the art that uses a prism. The present invention is also directed to methods for using the same. The sample holder device (10) includes a sample injection port (100), a prism retainer (200) and a sample compartment base (300). Unlike conventional SPR and PWR instruments that have a built-in sample chamber, the sample holder device (10) of the present invention provides a separate sample chamber that can be readily removed and replaced. Furthermore, by allowing ready replacement of the prism the sample holder device (10) of the invention allows user to fabricate custom sensor chips.

14 Claims, 9 Drawing Sheets

(58) Field of Classification Search
USPC ........................................................ 356/301
See application file for complete search history.

(56) References Cited

U.S. PATENT DOCUMENTS

| | | | |
|---|---|---|---|
| 5,991,488 A | 11/1999 | Salamon et al. | |
| 6,330,387 B1 | 12/2001 | Salamon et al. | |
| 6,421,128 B1 | 7/2002 | Salamon et al. | |
| 2002/0127706 A1 | 9/2002 | Naya et al. | |
| 2021/0349018 A1* | 11/2021 | Venkatarayalu | ..... G02B 6/4204 |

OTHER PUBLICATIONS

Isaacs, S. et al., Sensors, 2019, vol. 19, 1402.
Rascol, E. et al., Molecules, 2021, vol. 26, 6442.

* cited by examiner

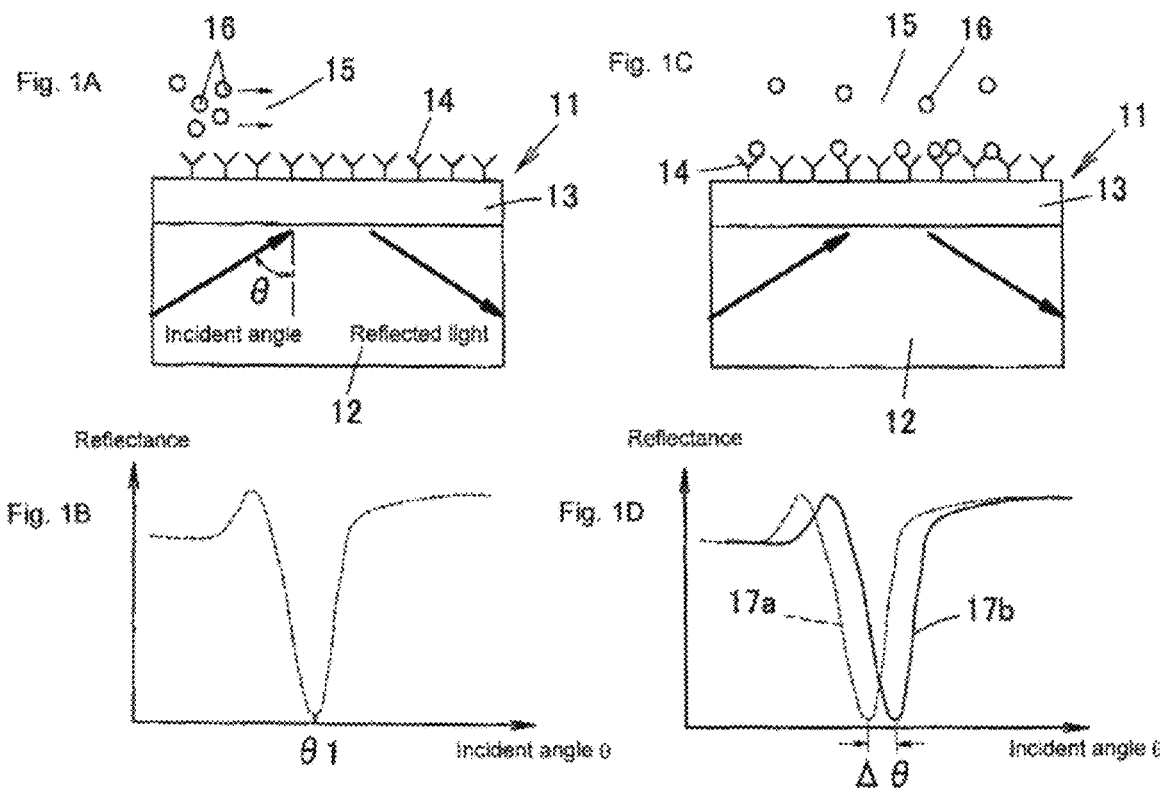
Fig. 1A
Fig. 1C
Fig. 1B
Fig. 1D
PRIOR ART
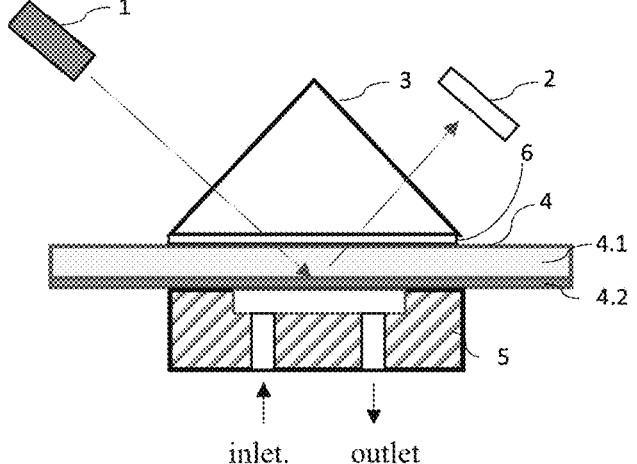
inlet. outlet
1 - Light Source; 2 – Detector; 3 – Prism; 4 – Sensor Chip (4.1 – glass substrate; 4.2 – metallic coating); 5 – Sample compartment; 6 – Optical glue
FIG. 2 (PRIOR ART)

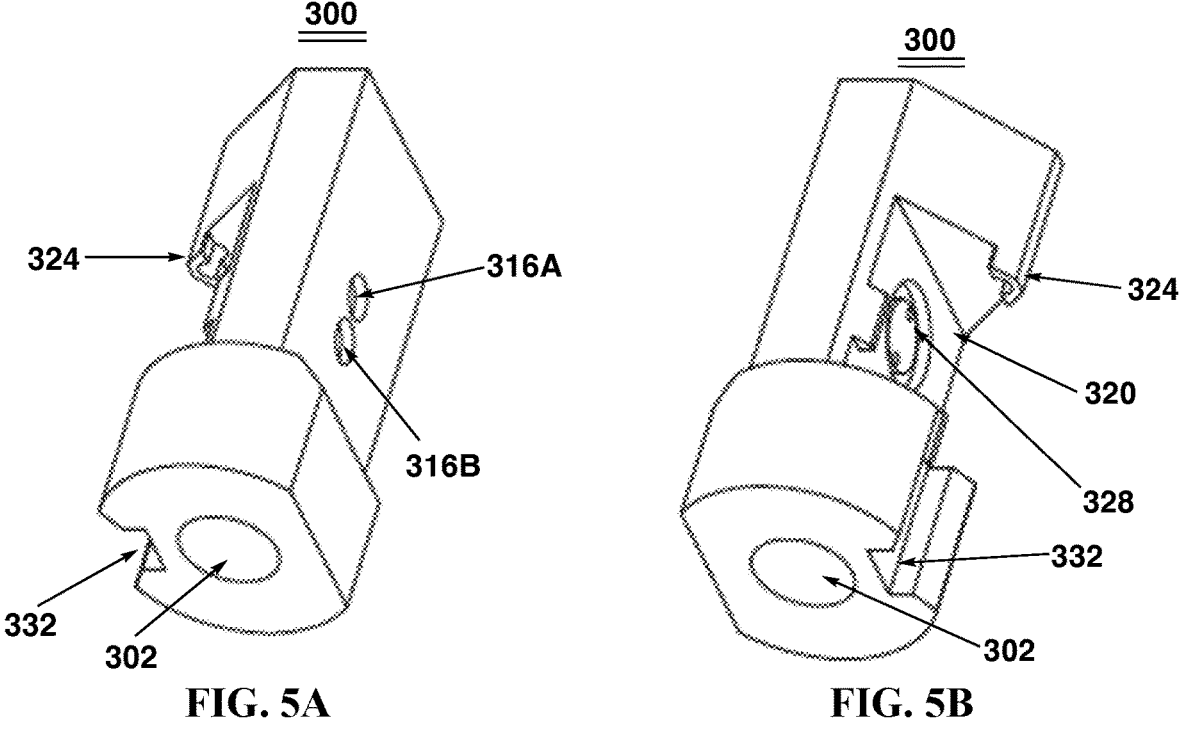
FIG. 5A                                              FIG. 5B
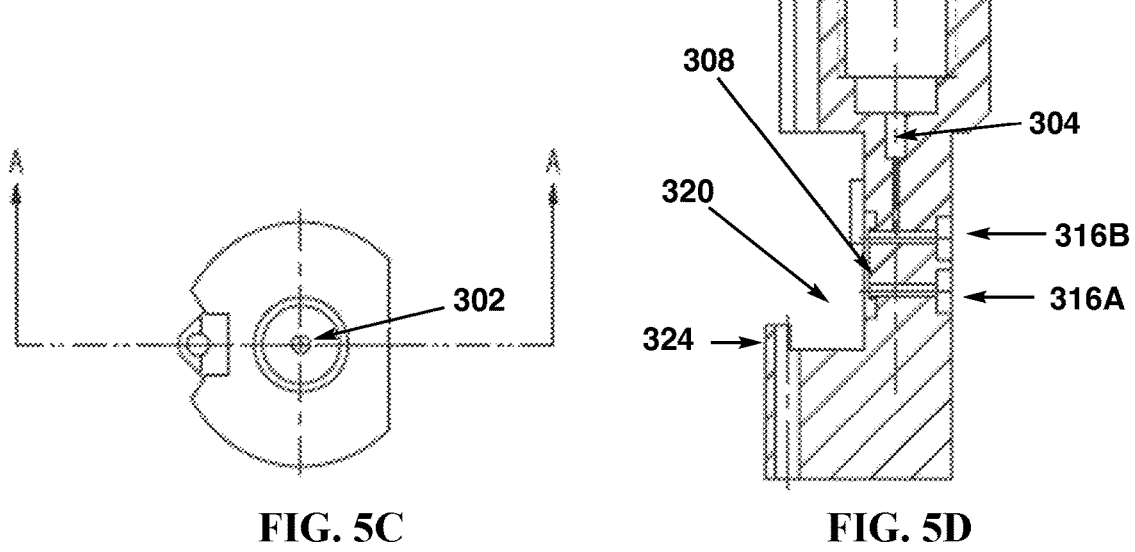
FIG. 5C                                              FIG. 5D

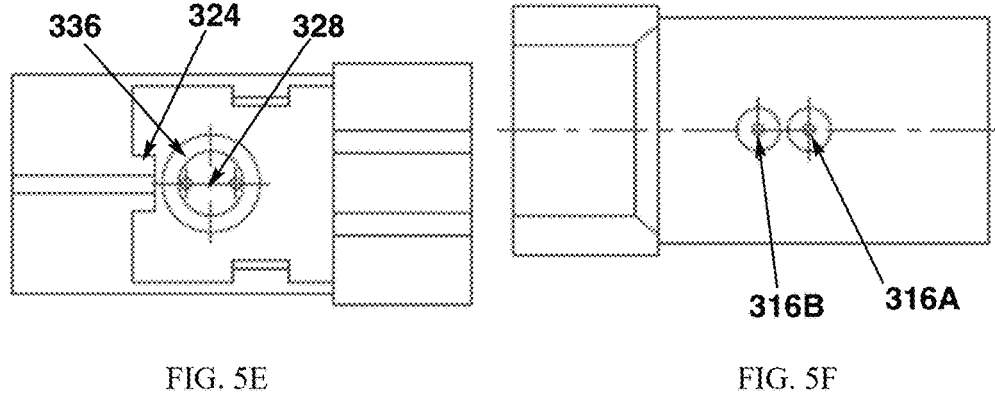
FIG. 5E                              FIG. 5F
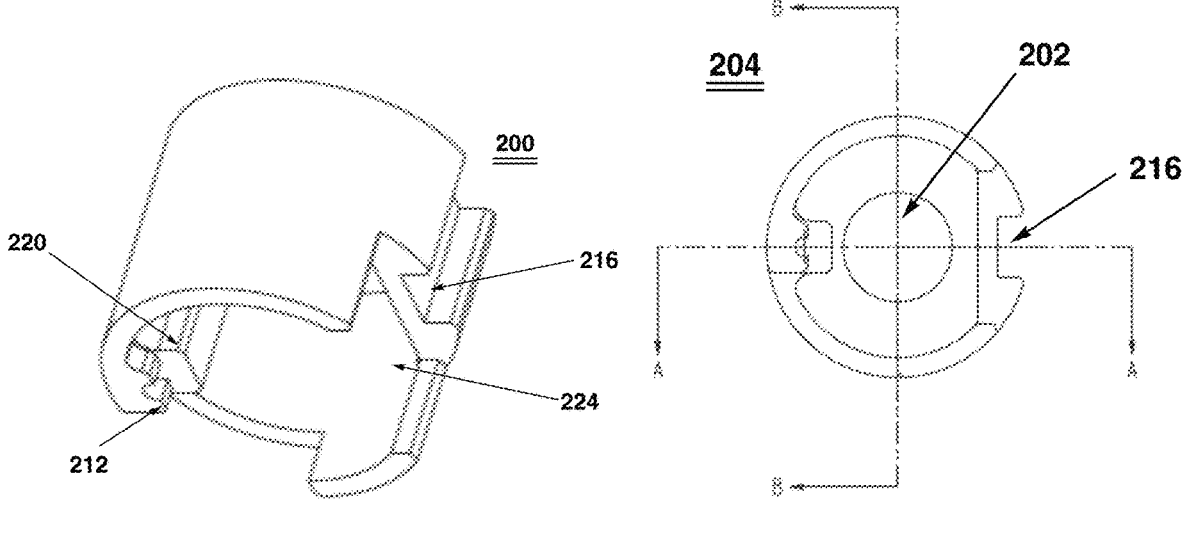
FIG. 6A                              FIG. 6B

SAMPLE HOLDER FOR SURFACE PLASMON RESONANCE AND PLASMON-WAVEGUIDE RESONANCE APPARATUS

FIELD OF THE INVENTION

The present invention relates to a removable sample holder for surface plasmon resonance (SPR) spectroscopy and plasmon-waveguide resonance (PWR) spectroscopic device and methods for using the same.

BACKGROUND OF THE INVENTION

The surface plasmon resonance (SPR) is a resonance phenomenon that occurs by interaction between free electrons of the metal surface and electromagnetic wave (light). SPR is a useful technique for observing small changes in the refractive index (RI). It is a powerful optical detection technique that allows observation of a label-free molecular interaction in realtime. As such, SPR has been used in a wide variety of applications, including in life sciences, electrochemistry, chemical vapor detection, food and environmental safety, chemical and biological sensing, drug development, material science, etc. Some of the key detections that can be made or observed using SPR are binding, kinetics, affinity, specificity, and concentration of a desired ligand, without any need for labels.

Plasmon waveguide resonance (PWR) is a variant of surface plasmon resonance. PWR possesses several advantages compared to SPR. In particular, typical signal peaks in PWR are narrower by almost an order of a magnitude than the comparable SPR. In addition, PWR utilizes the waveguide mode as opposed to the surface plasmon mode used by SPR. PWR also allows light in both polarizations to be utilized as opposed to just one polarization in SPR, and opens the door to measure optical anisotropy of thin layer of materials on the surface and determining the orientation of molecules with high resolution. This is one of the reasons why PWR is ideal for investigating molecular interactions occurring in anisotropic-oriented thin films, such as those in cell membranes.

The classical device by which SPR is carried out is known as the Kretschmann configuration. Briefly, a prism is used to introduce light to the glass substrate in a general propagation surface plasmon resonance sensor. The sensor chip (typically comprising a glass substrate coated with a conductor) and the prism need to be closely attached with a thin film or a matching oil. A sensor using surface plasmon resonance includes a propagation surface plasmon resonance sensor and a local surface plasmon resonance. The principle of the propagation surface plasmon resonance sensor is briefly described with references to FIGS. 1A to 1D, which are reproduced from U.S. Pat. No. 7,839,508. Briefly, referring to FIGS. 1A and 1C, the propagation surface plasmon resonance sensor (11) has a metal film (13) on the surface of a glass substrate (12). The surface plasmon resonance sensor (11) irradiates light from the glass substrate (12) side, and reflects the light at an interface of the glass substrate (12) and the metal film (13). The presence or the absence of a desired compound is determined by analyzing the reflected light and the reflectance of the light.

Reflectance measurement is carried out by changing the incident angle of the light. At a certain incident angle (resonance incident angle) θ1, as shown in FIG. 1B, the reflecting angle is greatly attenuated. When the light entering the interface of the glass substrate (12) and the metal film

(13) is totally reflected at the relevant interface, evanescent light (near-field light) generated at the relevant interface and the surface plasmon wave of the metal interact. At a specific wavelength or a specific incident angle, the energy of the light is absorbed into the metal film (13) and changed to vibration energy of the free electrons in the metal film (13), whereby the reflectance of the light significantly lowers.

The resonance condition depends on the dielectric constant (index of refraction) of the peripheral substances of the metal film (13), and thus is used as a method for detecting change in characteristics of the peripheral substances at high sensitivity. In particular, when used as a biosensor, an antibody (14, i.e., probe) that uniquely bonds with a specific protein (16, e.g., antigen) is immobilized on the surface of the metal film (13) in advance, as shown in FIG. 1A. If an antigen (16) that acts as a target is present in an introduced test sample (15), the antigen (16) and the antibody (14) binds, as shown in FIG. 1C. The index of refraction around the metal film (13) changes when the antigen (16) is bonded, and the resonance wavelength and the resonance incident angle change. Therefore, whether or not the antigen (16) is contained in the test sample (15) can be determined by measuring change in the resonance wavelength, change in the resonance incident angle, or temporal change in the resonance wavelength (when incident angle remains unchanged) and the resonance incident angle at before and after introducing the test sample (15). The concentration of the antigen (16) in the sample can also be determined.

FIG. 1D shows one example of a result of measuring the dependency of reflectance with respect to the incident angle. In FIG. 1D, a broken line shows a reflectance spectrum 17a before the test sample (15) is introduced, and a solid line shows a reflectance spectrum 17b after the test sample (15) is introduced and the antigen (16) is complexed to the antibody (14). Whether or not the test sample (15) contains the antigen (16) can be examined by measuring the change 40 in resonance incident angle at before and after the test sample (15) is introduced. Using SPR or PWR, a wide variety of information can be determined such as, but not limited to, the concentration of the antigen (16) in a test sample, the presence of a specific pathogenic agent, presence of disorder, kinetics of binding, affinity, as well as other useful interaction information.

In a typical prism based SPR, PWR and alike systems, a prism is used to introduce light to the glass substrate. Conventional PWR systems do not use disposable sensor chips. Instead, it uses a metallic-plated prism and introduces the samples directly into the prism surface. FIG. 2. As it is readily evident in FIG. 2, in conventional PWR systems the sample compartment (5) and coated prism (8) need to be removed for cleaning after each test.

Some conventional SPR, PWR and the like systems that have direct sample introduction to prism surface require cleaning of prism and sample compartment after each test to avoid cross contamination. Cleaning of prism and flow path is typically done manually and is time-consuming. Cleaning prism and sample compartment also require one to shut down and take apart of the instrument. This makes the system less efficient and impractical for high throughput applications.

The prism-based SPR, PWR and alike systems with disposable sensor chips typically use an optical glue to ensure maximum light coupling between prism and sensor chip. This has many disadvantages. First, applying optical glue is an additional operational step and requiring proper technique to ensure consistent quality. This introduces additional variables which could affect the test result. Second, cleaning the optical glue adds complexity in system design and operational workflow. Third, adding operation glue and ensuring appropriate coupling increase the complexity of system design and make the system larger. Other disadvantages of conventional SPR systems include, but not limited to, (1) the sample compartment and flow path are fixed in the instrument and can only be cleaned by built-in sample flow system, which cannot clean the flow path thoroughly; and (2) over time, the carry-cover will build up and may affect the performance. As a result, most existing SPR system requires frequent maintenance to clean the flow system (e.g., weekly or monthly).

Therefore, there is a need for a SPR or PWR system that simplifies the operational workflow and increase the test efficiency.

SUMMARY OF THE INVENTION

Some aspects of the invention are based on development by the present inventors of a unit that can be simply loaded into a PWR or SPR system as a sensor chip. In some embodiments, unlike conventional PWR or SPR systems that require gluing of a prism and a sensor chip prior to operation, devices of the invention do not require any optical glue. Accordingly, devices of the invention simplify the operational workflow and increase the test efficiency. Moreover, by eliminating the additional glass slide used in most SPR instruments, devices of the invention also simplify the design of the SPR or PWR instruments, e.g., by eliminating a need to worry about coupling between a sensor chip (e.g., glass slide) and a prism.

Some aspects of the invention provide a sample holder device (10) comprising a sample injection port (100) that is removably connected to a sample compartment base (300), wherein said sample injection port (100) comprises:
  a top portion (104) comprising a sample injection orifice (112) for introducing a fluid sample to said sample holder device (10);
  a bottom portion (108); and
  a body portion (116) extending from said top portion (104) to said bottom portion (108);
  a channel (120) within said body portion (116) extending from said sample injection orifice (112) to said bottom portion (108);
and wherein
said sample compartment base (300) comprises:
  a sample inlet port (304) connected to a sample chamber (308), wherein said sample inlet port (304) is operatively connected to said sample injection orifice (104) of said sample injection port (100) to allow introduction of a sample into said sample chamber (308);
  a solution outlet (316A) for introducing a solution to said sample chamber (308);
  a solution inlet (316B) for removing a solution from said sample chamber (308); and
  a prism retainer compartment (320), wherein said prism retainer compartment (320) comprises a protuberance (324) that is adapted to hold a prism in place during operation.
The sample holder devices of the invention can be used in various spectroscopy instruments including, but not limited to, for plasmon-waveguided resonance (PWR) spectroscopic device, surface plasmon resonance (SPR) spectroscopy, and any other spectroscopy instruments that utilize an electromagnetic radiation and a prism.

In some embodiments, the sample holder device (10) further comprising a prism retainer (200), wherein said prism retainer (200) comprises:
  a top portion (204); and
  a bottom portion (208) comprising a slotted opening (212) that is adapted to allow insertion of a prism and holding a prism in place during operation.
Still in other embodiments, said prism retainer further comprises a fluid influx/efflux notch or a slotted opening (224) adapted to allow access to said solution outlet (316A) and said solution inlet (316B). Yet in other embodiments, said sample compartment base (300) further comprises a prism retainer guide channel (332) and said prism retainer (200) further comprises a prism retainer guide (220), wherein said prism retainer guide (220) is configured to insert into or join with the prism retainer guide channel (332) of said sample compartment base (300). In further embodiments, said prism retainer (200) further comprises a sample holder guide groove (216) that is adapted to mate with a sample place holder of an SPR apparatus.

Yet in further embodiments, said top portion (104) of said sample injection port (100) comprises an annular cavity (124) adapted to assist in introducing a test sample into said sample compartment base (300).

In other embodiments, said sample injection port (100) further comprises a joining element (102), and said sample compartment base (300) further comprises a corresponding joining element (302) that is adapted to join with said joining element (102) of the sample injection port (100).

Still in further embodiments, said sample injection port (100) further comprise a seating element (106) that is adapted to be in contact with the sample compartment base (300) when said sample injection port (100) is joined with the sample compartment base (300). In other embodiments, said seating element (106) comprises an annular cavity (122). Yet in other embodiments, said annular cavity (122) comprises a removably inserted seal (504).

In other embodiments, said sample compartment base (300) further comprises a chamber window (328) and a cavity (336) that surrounds said chamber window (328). In some instances, a removably inserted seal (508), e.g., an o-ring, is present within said annular cavity (336). It should be appreciated that any method of providing a seal between the prism (400) and the chamber window (328) can be used. Furthermore, it should be appreciated that the cavity can be of any shape to fit the desired seal. Typically, the cavity shape will depend on the type and/or shape of seal used.

Other aspect of the invention provides a sample holder device (10) comprising a sample injection port (100), a prism retainer (200) and a sample compartment base (300), wherein:
  said sample injection port (100) comprises:
    a top portion (104) comprising a sample injection orifice (112) for introducing a fluid sample to said sample holder device (10);
    a bottom portion (108); and
    a body portion (116) extending from said top portion (104) to said bottom portion (108); and
    a channel (120) within said body portion (116) extending from said sample injection orifice (112) to said bottom portion (108),
  and wherein said prism retainer (200) is removably attached to said sample injection port (100) and to said sample compartment base (300), wherein said prism retainer (200) comprises:
    a top portion (204); and a bottom portion (208) comprising a slotted opening (212) that is adapted to allow insertion of a prism and holding a prism in place during operation, and wherein said sample compartment base (300) comprises:

a sample inlet port (304) connected to a sample chamber (308), wherein said sample inlet port (304) is operatively connected to said sample injection orifice (104) of said sample injection port (100) to allow introduction of a sample into said sample chamber (308);

a solution outlet (316A) for introducing a solution to said sample chamber (308);

a solution inlet (316B) for removing a solution from said sample chamber (308); and a prism retainer compartment (320), wherein said prism retainer compartment (320) comprises a protuberance (324) that is adapted to hold a prism in place during operation.

Still other aspect of the invention provides a method for analyzing a test sample using a surface plasmon resonance (SPR) instrument and any of the sample holder device (10) disclosed herein. In some embodiments, said method comprising:

placing a prism (400) into a prism retainer (200) of a sample holder device (10), wherein said prism (400) is coated with a thin-film of metal, and wherein said thin-film of metal comprises a binding molecule;

placing said sample holder device (10) on to the SPR instrument;

adding a test sample to the sample chamber (308) of said sample compartment base (300) through said sample injection orifice (112) of said sample injection port (100); and analyzing the test sample using the SPR instrument.

BRIEF DESCRIPTION OF THE DRAWINGS

FIG. 1A is a prior art illustration of the principle of the propagation surface plasmon resonance sensor showing angle of incident and angle of reflected light prior to change in the surface binding.

FIG. 1B is a prior art graph illustrating an angle of incidence vs. angle of reflectance as measured by an SPR instrument.

FIG. 1C is a prior art illustration showing change in angle of reflectance due to binding of ligand 15 to receptor 14 attached to the metal film surface.

FIG. 1D is a prior art illustration showing shifting of angle of reflectance measurement due to binding of ligand 15 to receptor 14.

FIG. 2 is a prior art schematic illustration showing a conventional prism based PWR system with disposable sensor chip (4).

FIG. 5A is a perspective view of one particular embodiment of a sample compartment base (300).

FIG. 5B is a front side perspective view of the sample compartment base (300) of FIG. 5A.

FIG. 5C is a top view of the sample compartment base (300) of FIG. 5A.

FIG. 5D is a cross-sectional side view of the sample compartment base (300) of FIG. 5C along lines A-A.

FIG. 5E is a front view of the sample compartment base (300) of FIG. 5A.

FIG. 5F is a back view of the sample compartment base (300) of FIG. 5A.

FIG. 6A is a perspective view of one particular embodiment of a prism retainer (200) of the invention.

FIG. 6B is a top view of the prism retainer (200) of FIG. 6A.

DETAILED DESCRIPTION OF THE INVENTION

Figure 3A:
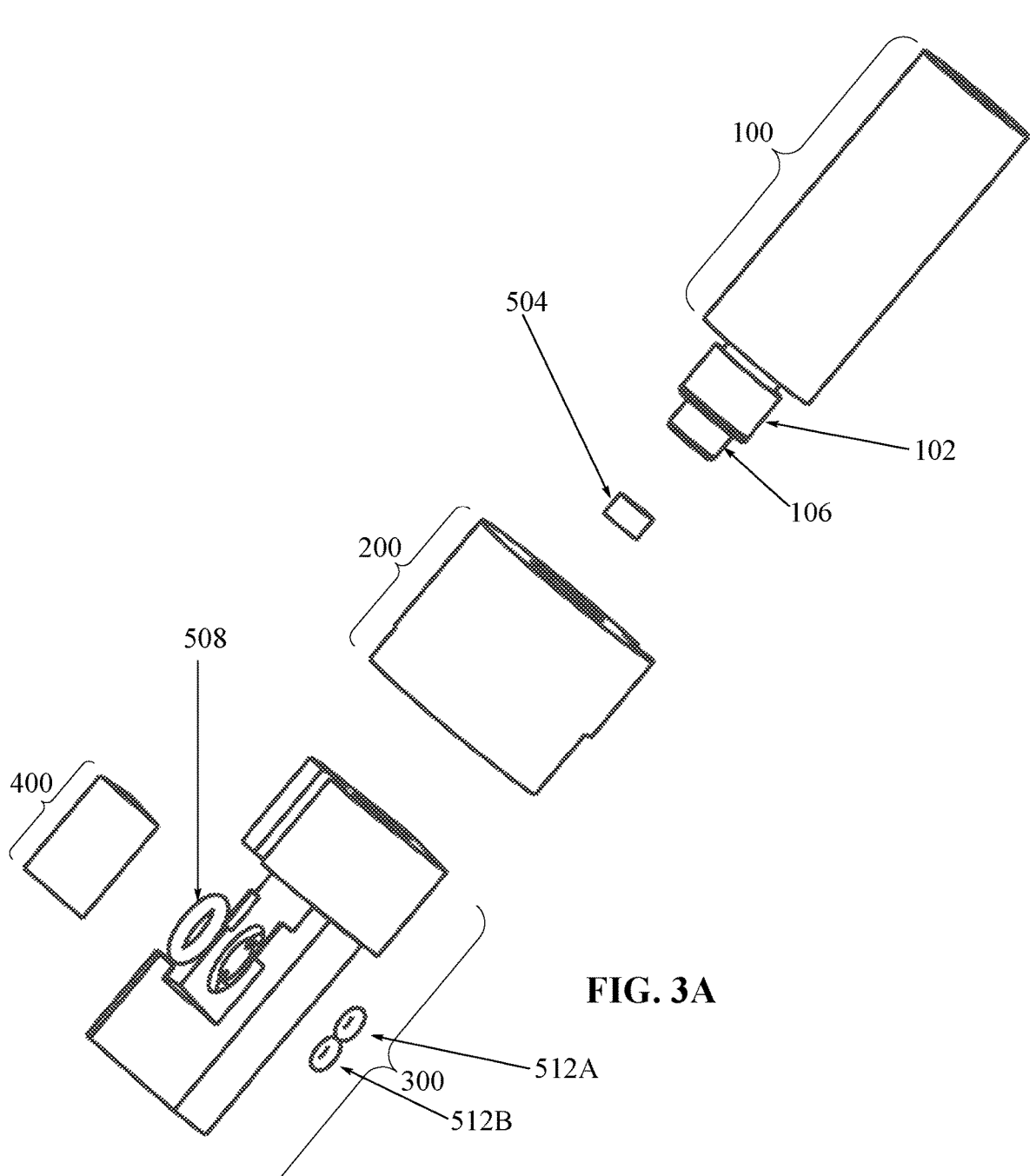
FIG. 3A is a perspective view of one particular embodiment of a sample holder device (10) of the invention.
Figure 3B:
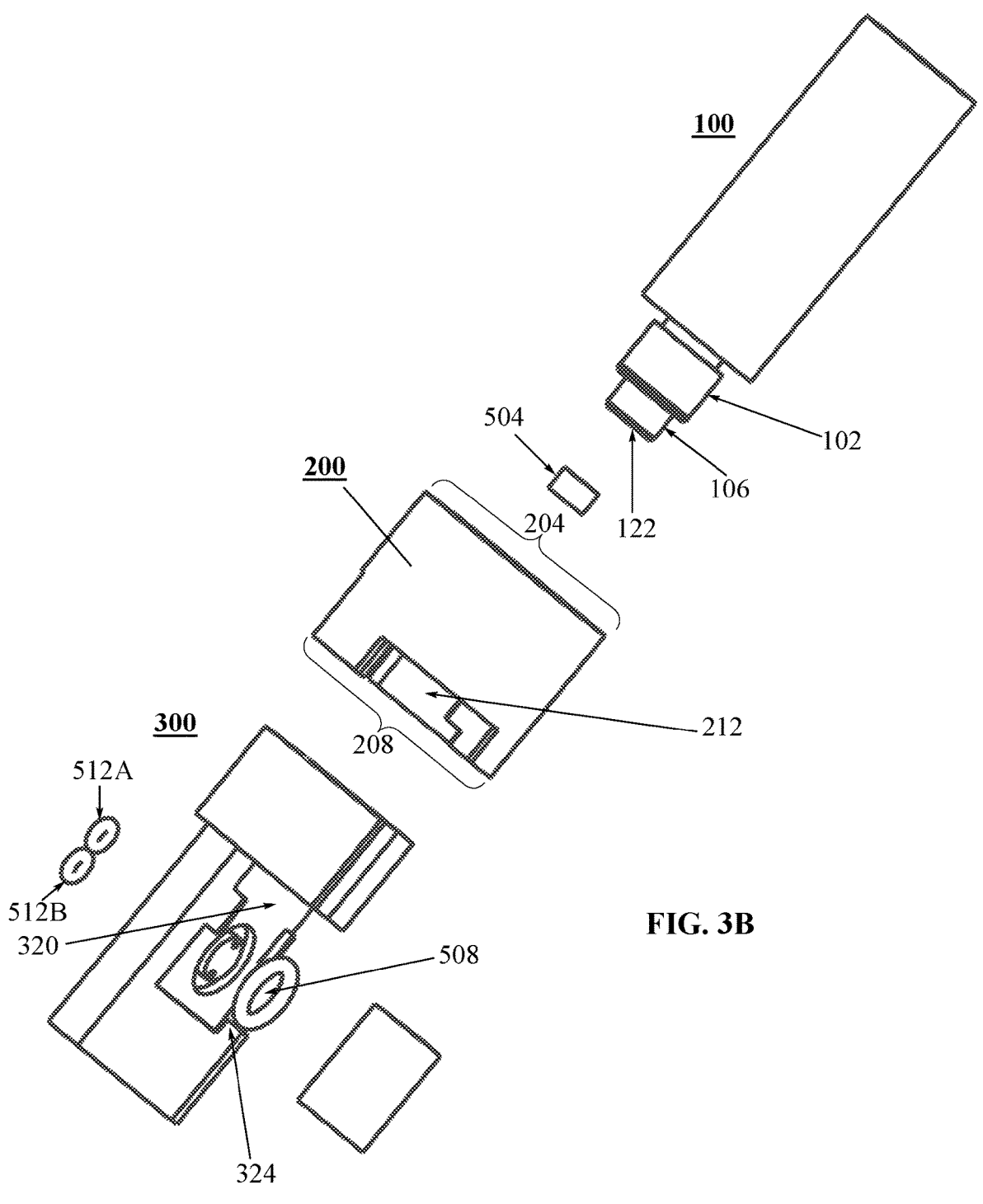
FIG. 3B is another perspective view of one particular embodiment of a sample holder device (10) of the invention with a rotated sample compartment base (300).
Figure 3C:
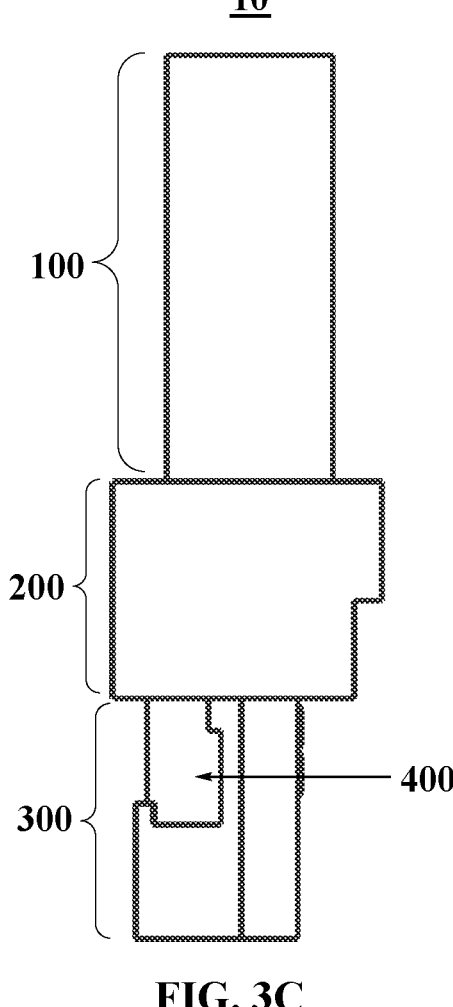
FIG. 3C shows one particular embodiment of a sample holder device (10) of the invention that is assembled.
Figure 3D:
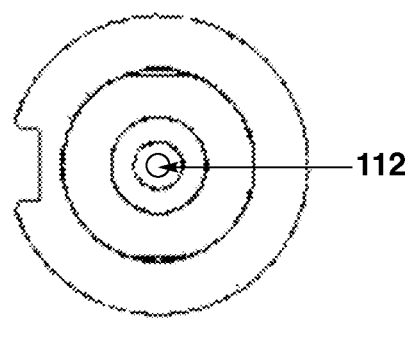
FIG. 3D is a top view of one particular embodiment of a sample holder device (10) of the invention.

The present invention will be described with regard to the accompanying drawings, which assist in illustrating various features of the invention. In this regard, the present invention relates to a sample holder device for spectroscopy instruments or apparatuses. The sample device of the invention is applicable for use in any instrument or spectroscopy apparatus that utilizes a prism and an electromagnetic radiation, such as but not limited to, plasmon-waveguided resonance (PWR) spectroscopy and surface plasmon resonance (SPR) spectroscopy. That is, in general the invention relates to a sample holder device for an analytical instrument that requires a prism and a sample chamber. For the sake of clarity and brevity, the present invention will now be described in reference to a sample holder for an SPR spectroscopy device. However, it should be appreciated that the scope of the invention is not limited to a sample holder for an SPR spectroscopy device. In fact, as stated above, methods and devices of the invention can be used generally in any device that requires a prism that is operationally connected or attached to a sample chamber, including but not limited to, PWR spectroscopy devices. Discussion of a sample holder for use in SPR apparatuses is provided solely for the purpose of illustrating the practice of the invention and do not constitute limitations on the scope thereof.

One particular embodiment of a sample holder for SPR or PWR is generally illustrated in FIGS. 3-6. It should be appreciated that this particular embodiment of the invention is provided solely for the purpose of illustrating the practice of the invention and does not constitute any limitations on the scope thereof.

As shown in FIGS. 3-6, a sample holder device (10) for plasmon-waveguided resonance (PWR) spectroscopic device or surface plasmon resonance (SPR) spectroscopy comprises a sample injection port (100), a prism holder (200) that is adapted for affixing a prism (400) in place, and a sample compartment base (300). In some embodiments, the sample injection port (100) and the prism holder (200) are a single unit.

Still in other embodiments, the sample injection port (100) is removably attached to the prism holder (200). In this manner, the sample injection port (100) can be removed and replaced with another sample injection port (100), e.g., for maintenance, thereby significantly reducing or eliminating the amount of time apparatus down time. The sample injection port (100) can be removably attached to the prism holder (200) by any of the means known to one skilled in the art, such as but not limited to, a lock-and-key mechanism, a quick release mechanism, threaded joint, snap-on mechanism, as well as other mechanisms for joining two elements of a device that are known to one skilled in the art. In one particular embodiment, the male-joining element (102) is threaded and is mated with the female-joining element (302) of the sample compartment base (300). In this manner, the sample injection port (100) can be easily removed, maintained, serviced (e.g., cleaned) or replaced. It should be appreciated that sample injection port (100) can be configured or designed differently than those shown to accommodate using different sample injection methods.

Figure 3E:
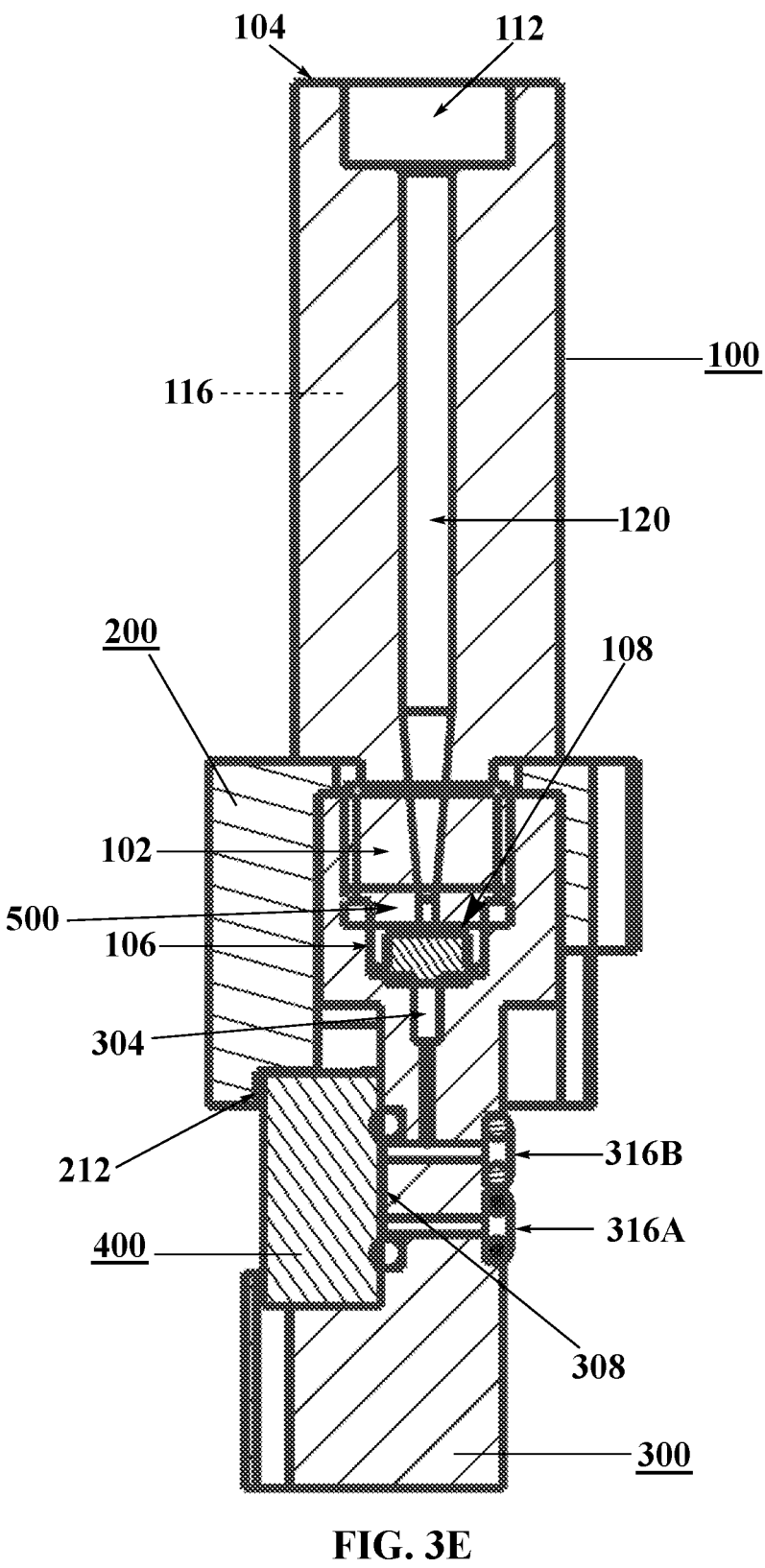
FIG. 3E is a mid-section cross-sectional view of FIG. 3D.

Referring in particular to FIGS. 4A-D, the sample injection port (100) comprises a top portion or top surface (104) comprising a sample injection orifice (112) for introducing a fluid sample to said sample holder device (10); a bottom portion or a bottom surface (108); and a body portion (116) extending from said top portion (104) to said bottom portion (108); a channel or a shaft (120) within said body portion (116) extending from said sample injection orifice (112) to said bottom portion (108). The shaft (120) is adapted to guide a needle or other means for injecting a test sample into the sample compartment base (300). The top portion (104) can optionally include an annular space or cavity (124) that can assist in inserting, injecting or introducing a test sample into sample compartment base (300). The body portion (116) can also include the male joining element (102) that is used to secure the sample injection port (100) to the female joining element (302) of the sample compartment base (300). While figures illustrate the male joining element (102) having a diameter smaller than the body portion (116), it should be appreciated that the diameter of the male joining element (102) can be equal to or even larger than the diameter of the body portion (116). The sample injection port (100) can also include a seating element (106) that has a smaller diameter than the male joining element (102) and is adapted to be in contact with the sample compartment base (300) when the sample injection port (100) is joined with the sample compartment base (300). The seating element (106) can also include an annular cavity or space (122). In general, the seating element (106) provides alignment of injection hole to sample compartment base (300). This annular cavity (122) can also be used to place a seal such as a septum (504) or any other sealing device known to one skilled in the art. This sealing device (504), e.g., a septum, allows syringe or other sample injection means to pierce through and inject or place a test sample into the sample chamber (308). FIG. 3E. The sealing device (500) also acts to prevent a test sample from leaking out of the sample chamber (308).

Referring in particular to FIGS. 5A-5F, the sample compartment base (300) includes a sample inlet port (304) connected to a sample chamber (308). As can be seen in FIG. 3E, the sample inlet port (304) is operatively connected to the sample injection orifice (112) of the sample injection port (100) to allow introduction of a test sample into the sample chamber (308). The sample chamber (308) can also include an annular cavity or a channel (336) that surrounds the chamber window (328). In this manner, a seal such as an o-ring (508), FIG. 3B, or other device can be inserted into the annular cavity (336) to provide sealing means between Prism (400) and sample compartment base (300) to avoid leakage.

Figure 4A:
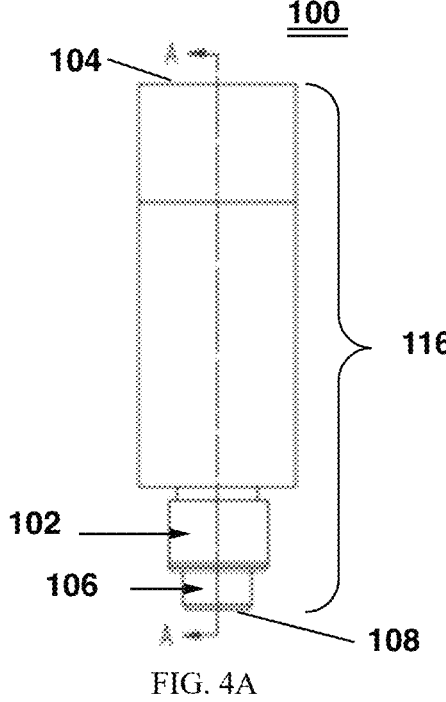
FIG. 4A is a one particular embodiment of a sample injection port (100).
Figure 4B:
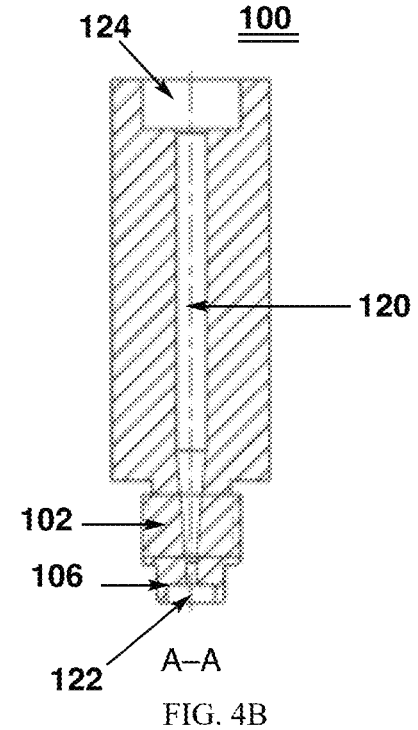
FIG. 4B is a cross-sectional view of FIG. 4A along the line A-A.
Figure 4C:
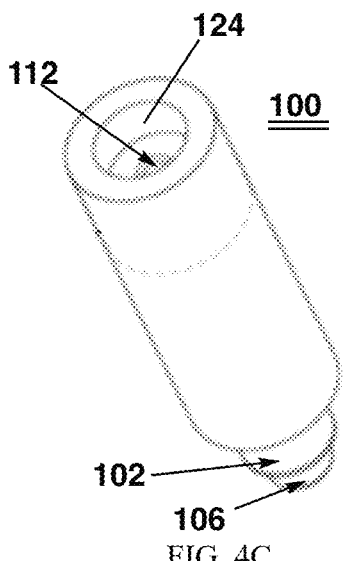
FIG. 4C is a perspective view of a sample injection port (100) of FIG. 4A.
Figure 4D:
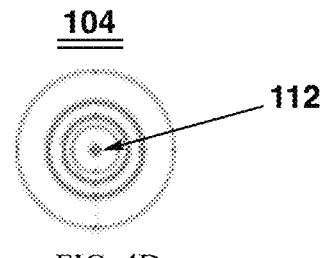
FIG. 4D is a top view of the sample injection port (100) of FIG. 4A.
Figures 6C, 6D:
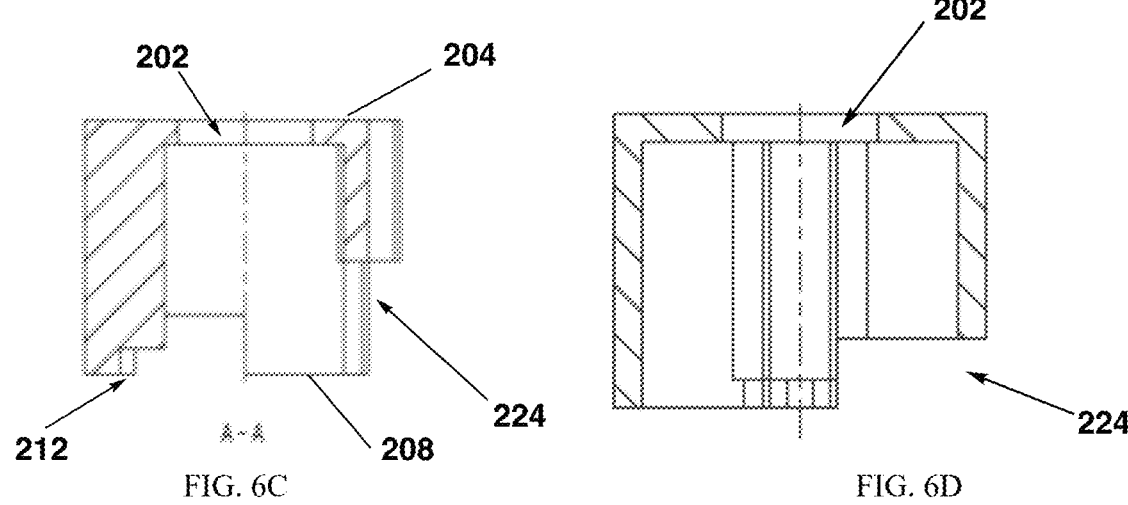
FIG. 6C is a cross-sectional view of the prism retainer (200) of FIG. 6B along lines A-A.
FIG. 6D is a cross-sectional view of the prism retainer (200) of FIG. 6B along lines B-B.

The sample compartment base (300) also includes a solution inlet (316B) for introducing a solution to the sample chamber (308) and a solution outlet (316A) for removing a solution from the sample chamber (308). The sample compartment base (300) also includes a prism retainer compartment (320) and a protuberance (324) that is adapted to hold a prism in place during operation. The protuberance (324) along with a prism retainer (200) infra aids in holding the prism (400) in place during operation. As can be seen in FIGS. 3E, 4B and 5D, a test sample, typically in solution, is introduced to the sample chamber (308) using, for example, a syringe or a cannula. In some embodiments, the sample compartment base (300) also includes a prism retainer guide channel (332). This guide channel (332) provides a means for guiding and properly placing the prism retainer (200) onto the sample compartment base (300).

The sample holder device (10) also includes a prism retainer (200). FIGS. 6A-6D. The prism retainer (200) can be formed of a single unit with the sample injection port (100). In such instances, the prism retainer guide channel (332) may be optional. In other embodiments, the prism retainer (200) is a separate device. The prism retainer (200) includes a top portion (204); and a bottom portion (208) comprising a slotted opening or a notch (212) that is adapted to allow insertion of a prism (400) and holding a prism (400) in place during operation. The prism retainer (200) also includes a fluid influx/efflux notch or a slotted opening (224) on the opposite side of the prism retainer slotted opening (212). The fluid influx/efflux notch (224) allows attachment of a solvent or a fluid distribution system. The fluid influx/efflux notch (224) allows access to the solution outlet (316A) and the solution inlet (316B) of the sample compartment base (300). In this manner a fluid, such as a solvent, a buffer solution, or a cleaning solution can be introduced to the sample chamber (308). The solution outlet (316A) and the solution inlet (316B) of the sample compartment base (300) can be recessed relative to the backside of the sample compartment base (300) as shown in FIG. 3E. This allows insertion of a seal such as an o-ring or other sealing devices (512A and 512B) known to one skilled in the art, see FIG. 3B, within the solution outlet (316A) and solution inlet (316B) to ensure tight seals between the sample compartment base (300) and a solution influx and efflux.

In some embodiments, the prism retainer (200) includes a prism retainer guide (220) that is configured to insert into or join with the prism retainer guide groove or channel (332) of the sample compartment base (300). This joining provides ease of alignment as well as a means for securely joining the prism retainer (200) with the sample compartment base (300). It should be appreciated that the prism retainer guide and the prism retainer guide groove can be reversed. That is the prism retainer guide groove can be present in the prism retainer (200) and the prism retainer guide can be present in the sample compartment base (300).

Yet in other embodiments, the prism retainer (200) can also include sample holder guide channel or groove (216) that is adapted to mate with a sample place holder of an PWR or the SPR apparatus (not shown). This allows one to affix the sample holder device (10) within the PWR or the SPR apparatus during operation.

The sample holder device (10) can be loaded or placed into a PWR or SPR apparatus as a sensor chip. Briefly, the sample holder device (10) is loaded or placed on a PWR or SPR apparatus to start a test. Unlike convention sample holder, the sample holder device (10) of the invention requires no optical glue. This simplifies the operational workflow and increases the test efficiency. In addition, the sample holder device (10) of the invention eliminates the need for additional sample glass slide used in most SPR instruments further allowing simplification of the design of the instrument as there is no need to worry about coupling between a sample glass slide and prism.

The sample holder device (10) includes a sample compartment base (300) that has integrated sample chamber (308) and flow paths (316A and 316B). A test sample is directly introduced through sample injection port (100) through the sample injection orifice (112) and does not share any flow path with any other solvents. When a new sample holder device (10) is loaded into the PWR or SPR apparatus, the entire sample flow path is replaced, thereby eliminating any possibility of cross contamination from a previous test sample. This design also reduces the maintenance need to the PWR or SPR apparatus or instrument flow path and down time. In addition, the sample holder device (10) of the invention simplifies the system design. For example, use of the sample holder device (10) of the invention eliminates the complicated hardware and software design for PWR or SPR instrument cleaning.

In most conventional SPR and PWR instruments or apparatuses, the sample flow path is built in the instruments and can only be cleaned through flushing process run by built-in sample flow system. Such a process cannot thoroughly clean the flow path. Over time, the minute carry-over samples from previously test samples will build up and affect the performance and/or the result of the SPR or PWR analysis. As a result, most conventional SPR and PWR instruments require frequent maintenance to thoroughly clean the flow system (e.g., weekly or monthly). Since the sample holder device (10) of the invention can be completely disassembled, thoroughly cleaning the every part of the unit is possible (e.g., using ultrasonic cleaning equipment, etc.). This simple maintenance allows the sample holder device (10) of the invention to be reused and significantly reduce or completely eliminate any potential carry-over from previous test samples. Ability to reuse the sample holder device (10) significantly reduces the cost per test.

Moreover, since the sample holder device (10) of the invention can be easily assembled and disassembled, every component of the unit can be separately removed for cleaning or maintenance. This makes the sample holder device (10) of the invention reuseable and extends the life of the device. Even when some parts the sample holder device (10) of the invention wears out after multiple cycles of cleaning (e.g., the prism may need re-coating), simply replacing that particular part instead of replacing the entire device significantly reduces the overall cost and down-time of the SPR or PWR apparatus. In addition, by allowing replacement of only those parts requiring replacement, the sample holder device (10) of the invention is also more environmentally friendly compared to conventional SPR or PWR instruments.

Furthermore, ease of assembly/disassembly also provides flexibility in sample testing applications. The prism (400) can be easily taken out and the surface of the prism (400) can be pre-treated (e.g., immobilize a specific antigen on the surface) before the test for different application purposes. This makes this chip (i.e., the prism (400)) more flexible and can be used for widely different applications. Most current state of the art sensor chips used in SPR are pre-coated in manufacturing phase. This pre-coating during the manufacturing makes it rather difficult to take glass slide out of a sensor chip for additional surface treatment once the chip is fabricated. This makes it impossible to custom treat the sensor chip by the user.

By integrating the coated-prism (400) as a separate unit from the sample compartment base (300) makes it possible to use the sample holder device (10) as a consumable device. Moreover, the sample holder guide channel or groove (216) that is present in the sample holder device (10) makes it easy to load or unload the sample holder device (10) from the SPR or PWR instrument.

Sample flow path (e.g., 308, 316A, and 316B) is integrated into the sample holder device (10) via the sample compartment base (300). Since the sample compartment base (300) can be easily removed and replaced from the sample holder device (10), it can be replaced from one sample test to another. This eliminates a need to clean the sample flow path for each sample test, which is required in conventional SPR and PWR instruments.

The sample holder device (10) of the invention is designed to allow the prism (400) to be easily positioned and locked for sample testing. This design makes the prism (400) to be easily removed and replaced.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A sample holder device (10) comprising a sample injection port (100) and a sample compartment base, wherein the sample injection port is removably connected to a sample compartment base (300), wherein said sample injection port (100) comprises:
  a top portion (104) comprising a sample injection orifice (112) for introducing a fluid sample to said sample holder device (10);
  a bottom portion (108); and
  a body portion (116) extending from said top portion (104) to said bottom portion (108);
  a channel (120) within said body portion (116) extending from said sample injection orifice (112) to said bottom portion (108);

and wherein
said sample compartment base (300) comprises:
  a sample inlet port (304) connected to a sample chamber (308), wherein said sample inlet port (304) is operatively connected to said sample injection orifice (112) (104) of said sample injection port (100) to allow introduction of a sample into said sample chamber (308);

a solution outlet (316A) for introducing a solution to said sample chamber (308);

a solution inlet (316B) for removing a solution from said sample chamber (308); and a prism retainer compartment (320), wherein said prism retainer compartment (320) comprises a protuberance (324) that is adapted to hold a prism in place during operation.

2. The sample holder device (10) of claim 1 further comprising a prism retainer (200), wherein said prism retainer (200) comprises:

a top portion (204); and a bottom portion (208) comprising a slotted opening (212) that is adapted to allow insertion of a prism and holding a prism in place during operation.

3. The sample holder device (10) of claim 2, wherein said prism retainer further comprises a fluid influx/efflux notch or a slotted opening (224) adapted to allow access to said solution outlet (316A) and said solution inlet (316B).

4. The sample holder device (10) of claim 2, wherein said prism retainer (200) further comprises a prism retainer guide channel (332) and said prism retainer (200) further comprises a prism retainer guide (220), wherein said prism retainer guide (220) is configured to insert into or join with the prism retainer guide channel (332) of said sample compartment base (300).

5. The sample holder device (10) of claim 2, wherein said prism retainer (200) further comprises a sample holder guide groove (216) that is adapted to mate with a sample place holder of an SPR apparatus.

6. The sample holder device (10) of claim 1, wherein said top portion (104) of said sample injection port (100) further comprises an annular cavity (124) adapted to assist in introducing a test sample into said sample compartment base (300).

7. The sample holder device (10) of claim 1, wherein said sample injection port (100) further comprises a joining element (102), and wherein said sample compartment base (300) further comprises a corresponding joining element (302) that is adapted to join with said joining element (102) of the sample injection port (100).

8. The sample holder device (10) of claim 1, wherein said sample injection port (100) further comprise a seating element (106) that is adapted to be in contact with the sample compartment base (300) when said sample injection port (100) is joined with the sample compartment base (300).

9. The sample holder device (10) of claim 8, wherein said seating element (106) comprises a cavity (122).

10. The sample holder device (10) of claim 9, wherein said cavity (122) comprises a removably inserted seal (504).

11. The sample holder device (10) of claim 1, wherein said sample compartment base (300) further comprises a chamber window (328) and a cavity (336) that surrounds said chamber window (328).

12. The sample holder device (10) of claim 11 further comprising a removably inserted seal (508) within said annular cavity (336).

13. A sample holder device (10) for plasmon-waveguided resonance (PWR) or surface plasmon resonance (SPR) spectroscopy, said device comprising a sample injection port (100), a prism retainer (200) and a sample compartment base (300), wherein said sample injection port is removably connected to said sample compartment base and said sample injection port comprises:

a top portion (104) comprising a sample injection orifice (112) for introducing a fluid sample to said sample holder device (10);

a bottom portion (108); and a body portion (116) extending from said top portion (104) to said bottom portion (108); and a channel (120) within said body portion (116) extending from said sample injection orifice (112) to said bottom portion (108), and wherein said prism retainer (200) is removably attached to said sample injection port (100) and to said sample compartment base (300), wherein said prism retainer (200) comprises:

a top portion (204); and a bottom portion (208) comprising a slotted opening (212) that is adapted to allow insertion of a prism and holding a prism in place during operation, and wherein said sample compartment base (300) comprises:

a sample inlet port (304) connected to a sample chamber (308), wherein said sample inlet port (304) is operatively connected to said sample injection orifice (112) of said sample injection port (100) to allow introduction of a sample into said sample chamber (308);

a solution outlet (316A) for introducing a solution to said sample chamber (308);

a solution inlet (316B) for removing a solution from said sample chamber (308); and a prism retainer compartment (320), wherein said prism retainer compartment (320) comprises a protuberance (324) that is adapted to hold a prism in place during operation.

14. A method for analyzing a test sample using a surface plasmon resonance (SPR) instrument, said method comprising:

placing a prism (400) into a prism retainer (200) of a sample holder device (10) of claim 13, wherein said prism (400) is coated with a thin-film of metal, and wherein said thin-film of metal comprises a binding molecule;

placing said sample holder device (10) on to the SPR instrument;

adding a test sample to the sample chamber (308) of said sample compartment base (300) through said sample injection orifice (112) of said sample injection port (100); and analyzing the test sample using the SPR instrument.

* * * * *